(12) United States Patent
Nakar et al.

(10) Patent No.: US 12,419,690 B2
(45) Date of Patent: Sep. 23, 2025

(54) SIGNAL ANALYSIS OF MOVEMENTS OF A REFERENCE ELECTRODE OF A CATHETER IN A CORONARY SINUS VEIN

(71) Applicant: Biosense Webster (Israel) Ltd., Yokneam (IL)

(72) Inventors: Elad Nakar, Timrat (IL); Lior Botzer, Timrat (IL); Jonathan Yarnitsky, Haifa (IL); Sigal Altman, Ramat Hashofet (IL); Dor Zeev Keren Tal, Harish (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 978 days.

(21) Appl. No.: 17/404,725

(22) Filed: Aug. 17, 2021

(65) Prior Publication Data

US 2022/0125523 A1    Apr. 28, 2022

Related U.S. Application Data

(60) Provisional application No. 63/104,214, filed on Oct. 22, 2020.

(51) Int. Cl.
   *A61B 34/20*    (2016.01)
   *A61B 5/00*     (2006.01)
   (Continued)

(52) U.S. Cl.
   CPC .............. *A61B 34/20* (2016.02); *A61B 5/068* (2013.01); *A61B 5/113* (2013.01); *A61B 5/7214* (2013.01); *A61B 2034/2046* (2016.02)

(58) Field of Classification Search
   CPC ........... A61B 34/20; A61B 5/068; A61B 5/06; A61B 5/113; A61B 5/7214;
   (Continued)

(56) References Cited

U.S. PATENT DOCUMENTS

| 6,216,027 B1 | 4/2001 | Willis et al. |
| 2004/0215139 A1 | 10/2004 | Cohen |

(Continued)

FOREIGN PATENT DOCUMENTS

WO    2012/082200 A1    6/2012

OTHER PUBLICATIONS

Nocedal et al., "Numerical Optimization," Germany, Springer New York—BFGS algorithm description, pp. 25, 31, 194-201, 219, 540, 550 (1999).

(Continued)

*Primary Examiner* — Keith M Raymond
*Assistant Examiner* — Milton Truong
(74) *Attorney, Agent, or Firm* — Frost Brown Todd LLP

(57) ABSTRACT

A method is provided. The method is implemented by a device orientation engine being executed by one or more processors. The method includes determining a movement between each electrode group of a catheter to provide movements and determining a total movement of electrodes of the catheter. The method also includes removing a standard component from the movements and the total movement and outputting a movement indication for the catheter based on the movements and the total movement with the standard component.

19 Claims, 12 Drawing Sheets

(51) Int. Cl.
*A61B 5/06* (2006.01)
*A61B 5/113* (2006.01)

(58) Field of Classification Search
CPC . A61B 2034/2046; A61B 5/367; A61B 5/339; A61B 5/7207
See application file for complete search history.

(56) References Cited

U.S. PATENT DOCUMENTS

| | | | |
|---|---|---|---|
| 2004/0254437 | A1 | 12/2004 | Hauck et al. |
| 2006/0106298 | A1 | 5/2006 | Ahmed et al. |
| 2006/0116575 | A1 | 6/2006 | Willis |
| 2006/0241401 | A1 | 10/2006 | Govari et al. |
| 2008/0082136 | A1 | 4/2008 | Gaudiani |
| 2008/0221643 | A1* | 9/2008 | Olson .................... A61B 5/287 702/19 |
| 2009/0265128 | A1* | 10/2009 | Markowitz ............ A61B 34/20 702/94 |
| 2009/0318995 | A1* | 12/2009 | Keel .................. A61N 1/36843 607/17 |
| 2010/0210938 | A1 | 8/2010 | Verard et al. |
| 2012/0157825 | A1* | 6/2012 | Koyrakh ................ A61B 5/063 600/424 |
| 2015/0366512 | A1* | 12/2015 | Koyrakh ................ A61B 5/063 600/547 |
| 2018/0200003 | A1 | 7/2018 | Olson |
| 2019/0285500 | A1* | 9/2019 | Budgett .................. A61B 5/03 |
| 2019/0365280 | A1 | 12/2019 | Shmayahu et al. |
| 2020/0289003 | A1 | 9/2020 | Hauck |

OTHER PUBLICATIONS

European Extended Search Report and Written Opinion dated Mar. 17, 2022, for Application No. 21203873.1, 8 pages.
European Communication dated Mar. 20, 2024, for Application No. 21203873.1, 6 pages.

* cited by examiner

SIGNAL ANALYSIS OF MOVEMENTS OF A REFERENCE ELECTRODE OF A CATHETER IN A CORONARY SINUS VEIN

CROSS-REFERENCE

This application claims the benefit of U.S. Provisional Patent Application No. 63/104,214 filed Oct. 22, 2020, which is incorporated by reference as if fully set forth.

FIELD OF INVENTION

The present invention is related to a method and system for signal processing. More particularly, the present invention relates to a signal analysis of movements of a reference electrode of a catheter in coronary sinus (CS) vein.

BACKGROUND

Currently, cardiac electrophysiology systems are used to map or visualize real-time calculated positions and orientations of a catheter within a patient's heart. In some cases, the cardiac electrophysiology systems utilize a reference point in time to visualize an activation wave on the heart, from beat to beat and/or for each point taken during a mapping process. Further, the cardiac electrophysiology systems can track time about the reference point.

Generally, the CS vein is an excellent reference point for the cardiac electrophysiology systems because the CS vein is between an atrium and a ventricle (e.g., meaning that a catheter can monitor both atria and ventricle activity). The CS vein is also optimal for reference point as the CS vein is a stable location to place the catheter and expect the catheter to maintain a same position throughout mapping. As cardiac electrophysiology systems rely on electrodes of a catheter as reference points within the CS, it is important that the electrodes do not move. When the reference electrodes within the CS move, it essentially hinders the accuracy of all measurements and further mapping should not take place. In particular, if the electrodes move, a timing of atrial tachycardia (AT) measurements or ventricular tachycardia (VT) measurements become unreliable and must be re-mapped, which prolongs the procedure.

There are presently no techniques that improve electrode/catheter stability and/or account for movement thereof. Such a technique may be beneficial for cardiac electrophysiology systems.

SUMMARY

According to an embodiment, a method is provided. The method is implemented by a device orientation engine being executed by one or more processors. The method includes determining a movement between each electrode group of a catheter to provide movements and determining a total movement of electrodes of the catheter. The method also includes removing a standard component from the movements and the total movement and outputting a movement indication for the catheter based on the movements and the total movement with the standard component.

According to one or more embodiments, the method embodiment above can be implemented as an apparatus, a system, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Figure 1:
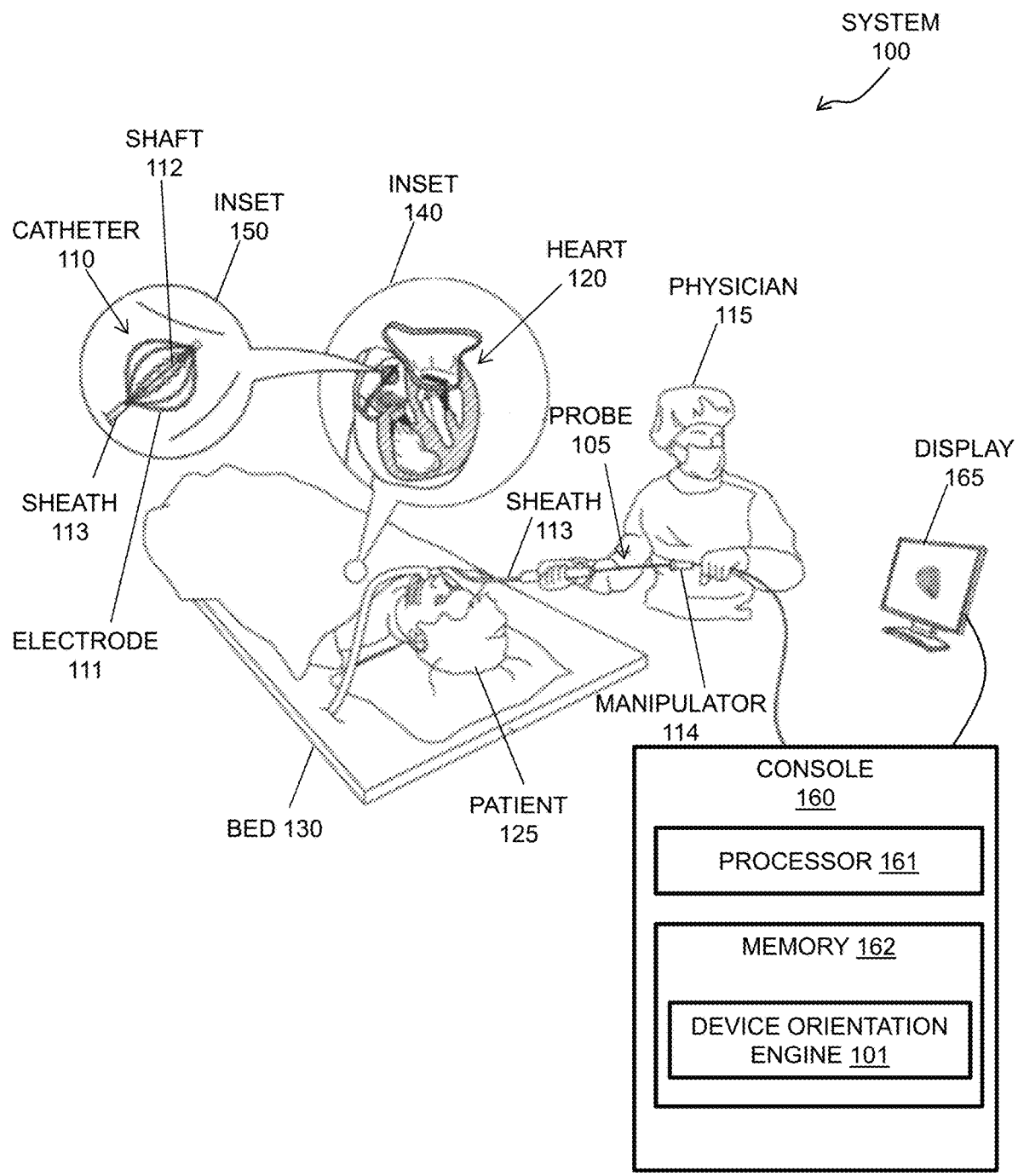
FIG. 1 illustrates a diagram of an exemplary system in which one or more features of the disclosure subject matter can be implemented according to one or more embodiments.

Disclosed herein is a method and system for signal processing. More particularly, the present invention relates to a signal analysis of movements of a reference electrode of a catheter in coronary sinus (CS) vein.

For example, a device orientation engine is a processor executable code or software that is necessarily rooted in process operations by, and in processing hardware of, medical device equipment. According to an exemplary embodiment, device orientation engine can include machine learning/artificial intelligence (ML/AI) algorithms. The device orientation engine tracks movements of a CS catheter within the CS while mapping the CS. For instance, the device orientation engine tracks movements of the CS catheter along an axial axis of the CS, which may affect a stability of a reference of a map, and tracks deviations from an acquired reference position at a beginning of mapping.

The technical effects and benefits of the device orientation engine include providing cardiac physicians and medical personnel a visual representation of an original catheter position in relation to a displaced catheter position following inadvertent catheter movements. Thus, the device orientation engine particularly utilizes and transforms medical device equipment to enable/implement CS catheter displacement estimations that are otherwise not currently available or currently performed by cardiac electrophysiology systems.

According to one or more embodiments, the device orientation engine being executed by one or more processors implements a method. The method includes determining a movement between each electrode group of a catheter to provide movements and determining a total movement of electrodes of the catheter. The method also includes removing a standard component from the movements and the total movement and outputting a movement indication for the catheter based on the movements and the total movement with the standard component.

According to one or more embodiments or any of the method embodiments herein, the device orientation engine can utilize positions per timestamp for electrodes of each electrode group and a reference position as inputs for determining the movement between each electrode group.

According to one or more embodiments or any of the method embodiments herein, the movement between each electrode group can be determined based on at least a set of two vectors constructed for each electrode group.

According to one or more embodiments or any of the method embodiments herein, the movement between each electrode group can be determined based on a third vector between the set of two vectors for each electrode group.

According to one or more embodiments or any of the method embodiments herein, the total movement can be based on an average movement of three median electrode pairs of the plurality of electrodes.

According to one or more embodiments or any of the method embodiments herein, the processor executable code can further be executed to cause the system to determine a median value for each movement between each electrode pair; select three movement measurements nearest to the median value to provide selected measurements; and determine an average value for the selected measurements to provide the average movement.

According to one or more embodiments or any of the method embodiments herein, the standard component can include respiration movement or heartbeat movement.

According to one or more embodiments or any of the method embodiments herein, the movement indication can be for every input position compared against a reference position.

According to one or more embodiments or any of the method embodiments herein, movement indication can be along an axial insertion axis of the catheter into a coronary sinus.

According to one or more embodiments, a system comprises a memory and one or more processors. The memory stores processor executable code for a device orientation engine. The one or more processors executes the processor executable code to cause the system and the device orientation engine to determine a movement between each electrode group of a catheter to provide movements and determine a total movement of electrodes of the catheter. The processor executable code further causes the system and the device orientation engine to remove a standard component from the movements and the total movement and output a movement indication for the catheter based on the movements and the total movement with the standard component.

According to one or more embodiments or any of the system embodiments herein, the device orientation engine can utilize positions per timestamp for electrodes of each electrode group and a reference position as inputs for determining the movement between each electrode group.

According to one or more embodiments or any of the system embodiments herein, the movement between each electrode group can be determined based on at least a set of two vectors constructed for each electrode group.

According to one or more embodiments or any of the system embodiments herein, the movement between each electrode group can be determined based on a third vector between the set of two vectors for each electrode group.

According to one or more embodiments or any of the system embodiments herein, the total movement can be based on an average movement of three median electrode pairs of the plurality of electrodes.

According to one or more embodiments or any of the system embodiments herein, the processor executable code can further be executed to cause the system to determine a median value for each movement between each electrode pair; select three movement measurements nearest to the median value to provide selected measurements; and determine an average value for the selected measurements to provide the average movement.

According to one or more embodiments or any of the system embodiments herein, the standard component can include respiration movement or heartbeat movement.

According to one or more embodiments or any of the system embodiments herein, the movement indication can be for every input position compared against a reference position.

According to one or more embodiments or any of the system embodiments herein, movement indication can be along an axial insertion axis of the catheter into a coronary sinus.

According to one or more embodiments or any of the system embodiments herein, the catheter can be a linear catheter.

FIG. 1 is a diagram of a system 100 (e.g., medical device equipment) in which one or more features of the subject matter herein can be implemented according to one or more embodiments. All or part of the system 100 can be used to collect information (e.g., biometric data and/or a training dataset) and/or used to implement a device orientation engine 101, as described herein.

The system 100, as illustrated, includes a probe 105 with a catheter 110 (including at least one electrode 111), a shaft 112, a sheath 113, and a manipulator 114. The system 100, as illustrated, also includes a physician 115 (or a medical professional, clinician, technician, or the like), a heart 120, a patient 125, and a bed 130 (or a table). Note that insets 140 and 150 show the heart 120 and the catheter 110 in greater detail. The system 100 also, as illustrated, includes a console 160 (including one or more processors 161 and memories 162) and a display 165. Note further each element and/or item of the system 100 is representative of one or more of that element and/or that item. The example of the system 100 shown in FIG. 1 can be modified to implement the embodiments disclosed herein. The disclosed embodiments can similarly be applied using other system components and settings. Additionally, the system 100 can include additional components, such as elements for sensing electrical activity, wired or wireless connectors, processing and display devices, or the like.

The system 100 can be utilized to detect, diagnose, and/or treat cardiac conditions (e.g., using the device orientation engine 101). Cardiac conditions, such as cardiac arrhythmias, persist as common and dangerous medical ailments, especially in the aging population. For instance, the system 100 can be part of a surgical system (e.g., Carto® system sold by Biosense Webster) that is configured to obtain biometric data (e.g., anatomical and electrical measurements of a patient's organ, such as the heart 120) and perform a cardiac ablation procedure.

In patients (e.g., the patient 125) with normal sinus rhythm (NSR), the heart (e.g., the heart 120), which includes atrial, ventricular, and excitatory conduction tissue, is electrically excited to beat in a synchronous, patterned fashion.

Note that this electrical excitement can be detected as intracardiac electrocardiogram (IC ECG) data or the like.

In patients (e.g., the patient 125) with a cardiac arrhythmia (e.g., atrial fibrillation or aFib), abnormal regions of cardiac tissue do not follow a synchronous beating cycle associated with normally conductive tissue, which is in contrast to patients with NSR. Instead, the abnormal regions of cardiac tissue aberrantly conduct to adjacent tissue, thereby disrupting the cardiac cycle into an asynchronous cardiac rhythm. Note that this asynchronous cardiac rhythm can also be detected as the IC ECG data. Such abnormal conduction has been previously known to occur at various regions of the heart 120, for example, in the region of the sino-atrial (SA) node, along the conduction pathways of the atrioventricular (AV) node, or in the cardiac muscle tissue forming the walls of the ventricular and atrial cardiac chambers.

In support of the system 100 detecting, diagnosing, and/or treating cardiac conditions, the probe 105 can be navigated by the physician 115 into the heart 120 of the patient 125 lying on the bed 130. For instance, the physician 115 can insert the shaft 112 through the sheath 113, while manipulating a distal end of the shaft 112 using the manipulator 114 near the proximal end of the catheter 110 and/or deflection from the sheath 113. As shown in an inset 140, the catheter 110 can be fitted at the distal end of the shaft 112. The catheter 110 can be inserted through the sheath 113 in a collapsed state and can be then expanded within the heart 120.

The catheter 110, which can include the at least one electrode 111 and a catheter needle coupled onto a body thereof, can be configured to obtain biometric data, such as electrical signals of an intra-body organ (e.g., the heart 120), and/or to ablate tissue areas of thereof (e.g., a cardiac chamber of the heart 120). Note that the electrodes 111 are representative of any like elements, such as tracking coils, piezoelectric transducer, electrodes, or combination of elements configured to ablate the tissue areas or to obtain the biometric data. According to one or more embodiments, the catheter 110 can include one or more position sensors that used are to determine trajectory information. The trajectory information can be used to infer motion characteristics, such as the contractility of the tissue.

Biometric data (e.g., patient biometrics, patient data, or patient biometric data) can include one or more of local time activations (LATs), electrical activity, topology, bipolar mapping, dominant frequency, impedance, or the like. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts. A dominant frequency can be a frequency or a range of frequency that is prevalent at a portion of a body part and can be different in different portions of the same body part. For example, the dominant frequency of a PV of a heart can be different than the dominant frequency of the right atrium of the same heart. Impedance can be the resistance measurement at a given area of a body part.

Examples of biometric data include, but are not limited to, patient identification data, IC ECG data, anatomical and electrical measurements, trajectory information, body surface (BS) ECG data, historical data, brain biometrics, blood pressure data, ultrasound signals, radio signals, audio signals, a two- or three-dimensional image data, blood glucose data, and temperature data. The biometrics data can be used, generally, to monitor, diagnosis, and treatment any number of various diseases, such as cardiovascular diseases (e.g., arrhythmias, cardiomyopathy, and coronary artery disease) and autoimmune diseases (e.g., type I and type II diabetes). Note that BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

For example, the catheter 110 can use the electrodes 111 to implement intravascular ultrasound and/or MRI catheterization to image the heart 120 (e.g., obtain and process the biometric data). Inset 150 shows the catheter 110 in an enlarged view, inside a cardiac chamber of the heart 120. Although the catheter 110 is shown to be a point catheter, it will be understood that any shape that includes one or more electrodes 111 can be used to implement the embodiments disclosed herein.

Examples of the catheter 106 include, but are not limited to, a linear catheter with multiple electrodes, a balloon catheter including electrodes dispersed on multiple spines that shape the balloon, a lasso or loop catheter with multiple electrodes, or any other applicable shape. Linear catheters can be fully or partially elastic such that it can twist, bend, and or otherwise change its shape based on received signal and/or based on application of an external force (e.g., cardiac tissue) on the linear catheter. The balloon catheter can be designed such that when deployed into a patient's body, its electrodes can be held in intimate contact against an endocardial surface. As an example, a balloon catheter can be inserted into a lumen, such as a pulmonary vein (PV). The balloon catheter can be inserted into the PV in a deflated state, such that the balloon catheter does not occupy its maximum volume while being inserted into the PV. The balloon catheter can expand while inside the PV, such that those electrodes on the balloon catheter are in contact with an entire circular section of the PV. Such contact with an entire circular section of the PV, or any other lumen, can enable efficient imaging and/or ablation.

The probe 105 and other items of the system 100 can be connected to the console 160. The console 160 can include any computing device, which can employ ML/AI algorithms of the device orientation engine 101. According to an embodiment, the console 160 includes the one or more processors 161 (any computing hardware) and the memory 162 (any non-transitory tangible media), where the one or more processors 161 execute computer instructions with respect the device orientation engine 101 and the memory 162 stores these instructions for execution by the one or more processors 161. For instance, the console 160 can be configured to receive and process the biometric data and determine if a given tissue area conducts electricity. In some embodiments, the console 160 can be further programmed by the device orientation engine 101 (in software) to carry out the functions of determining a movement between each electrode group of a catheter to provide movements; determining a total movement of electrodes of the catheter; removing a standard component from the movements and the total movement; and outputting a movement indication for the catheter based on the movements and the total movement with the standard component. According to one or more embodiments, the device orientation engine 101 can be external to the console 160 and can be located, for example, in the catheter 110, in an external device, in a mobile device, in a cloud-based device, or can be a stand-alone processor. In this regard, the device orientation engine 101 can be transferable/downloaded in electronic form, over a network.

In an example, the console 160 can be any computing device, as noted herein, including software (e.g., the device orientation engine 101) and/or hardware (e.g., the processor 161 and the memory 162), such as a general-purpose computer, with suitable front end and interface circuits for transmitting and receiving signals to and from the probe 105, as well as for controlling the other components of the system 100. For example, the front end and interface circuits include input/output (I/O) communication interfaces that enables the console 160 to receive signals from and/or transfer signals to the at least one electrode 111. The console 160 can include real-time noise reduction circuitry typically configured as a field programmable gate array (FPGA), followed by an analog-to-digital (A/D) ECG or electrocardiograph/electromyogram (EMG) signal conversion integrated circuit. The console 160 can pass the signal from an A/D ECG or EMG circuit to another processor and/or can be programmed to perform one or more functions disclosed herein.

The display 165, which can be any electronic device for the visual presentation of the biometric data, is connected to the console 160. According to an embodiment, during a procedure, the console 160 can facilitate on the display 165 a presentation of a body part rendering to the physician 115 and store data representing the body part rendering in the memory 162. For instance, maps depicting motion characteristics can be rendered/constructed based on the trajectory information sampled at a sufficient number of points in the heart 120. As an example, the display 165 can include a touchscreen that can be configured to accept inputs from the physician 115, in addition to presenting the body part rendering.

In some embodiments, the physician 115 can manipulate the elements of the system 100 and/or the body part rendering using one or more input devices, such as a touch pad, a mouse, a keyboard, a gesture recognition apparatus, or the like. For example, an input device can be used to change a position of the catheter 110, such that rendering is updated. Note that the display 165 can be located at a same location or a remote location, such as a separate hospital or in separate healthcare provider networks.

According to one or more embodiments, the system 100 can also obtain the biometric data using ultrasound, computed tomography (CT), MRI, or other medical imaging techniques utilizing the catheter 110 or other medical equipment. For instance, the system 100 can obtain ECG data and/or anatomical and electrical measurements of the heart 120 (e.g., the biometric data) using one or more catheters 110 or other sensors. More particularly, the console 160 can be connected, by a cable, to BS electrodes, which include adhesive skin patches affixed to the patient 125. The BS electrodes can procure/generate the biometric data in the form of the BS ECG data. For instance, the processor 161 can determine position coordinates of the catheter 110 inside the body part (e.g., the heart 120) of the patient 125. The position coordinates may be based on impedances or electromagnetic fields measured between the body surface electrodes and the electrode 111 of the catheter 110 or other electromagnetic components. Additionally, or alternatively, location pads may be located on a surface of the bed 130 and may be separate from the bed 130. The biometric data can be transmitted to the console 160 and stored in the memory 162. Alternatively, or in addition, the biometric data may be transmitted to a server, which may be local or remote, using a network as further described herein.

According to one or more embodiments, the catheter 110 may be configured to ablate tissue areas of a cardiac chamber of the heart 120. Inset 150 shows the catheter 110 in an enlarged view, inside a cardiac chamber of the heart 120. For instance, ablation electrodes, such as the at least one electrode 111, may be configured to provide energy to tissue areas of an intra-body organ (e.g., the heart 120). The energy may be thermal energy and may cause damage to the tissue area starting from the surface of the tissue area and extending into the thickness of the tissue area. The biometric data with respect to ablation procedures (e.g., ablation tissues, ablation locations, etc.) can be considered ablation data.

Figure 2:
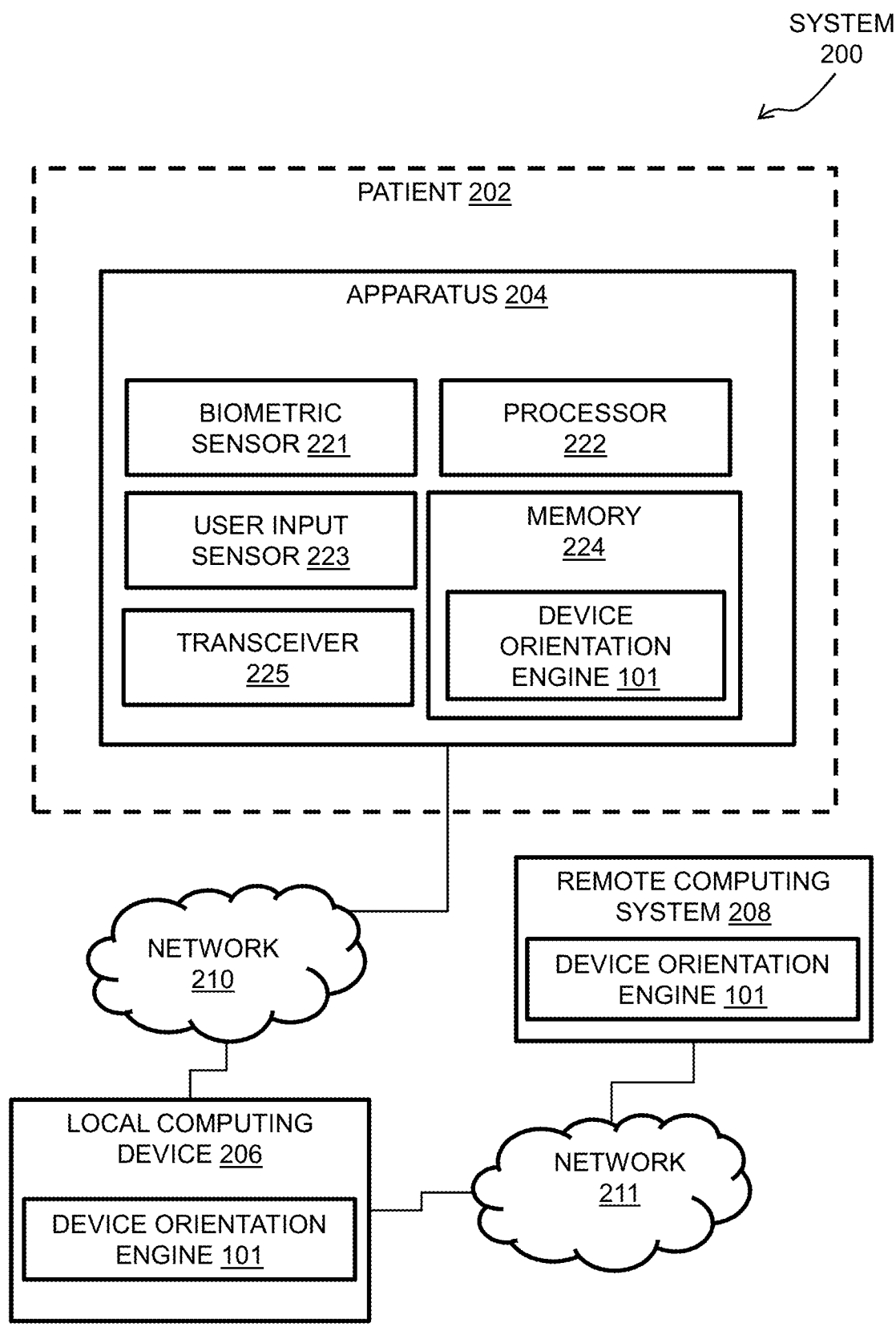
FIG. 2 illustrates a block diagram of an example system for signal analysis of movement of reference electrode of a catheter in coronary sinus (CS) vein according to one or more embodiments.

Turning now to FIG. 2, a diagram of a system 200 in which one or more features of the disclosure subject matter can be implemented is illustrated according to one or more embodiments. The system 200 includes, in relation to a patient 202 (e.g., an example of the patient 125 of FIG. 1), an apparatus 204, a local computing device 206, a remote computing system 208, a first network 210, and a second network 211. Further, the apparatus 204 can include a biometric sensor 221 (e.g., an example of the catheter 110 of FIG. 1), a processor 222, a user input (UI) sensor 223, a memory 224, and a transceiver 225. Note that the device orientation engine 101 of FIG. 1 is reused in FIG. 2 for ease of explanation and brevity.

According to an embodiment, the apparatus 204 can be an example of the system 100 of FIG. 1, where the apparatus 204 can include both components that are internal to the patient and components that are external to the patient. According to an embodiment, the apparatus 204 can be an apparatus that is external to the patient 202 that includes an attachable patch (e.g., that attaches to a patient's skin). According to another embodiment, the apparatus 204 can be internal to a body of the patient 202 (e.g., subcutaneously implantable), where the apparatus 204 can be inserted into the patient 202 via any applicable manner including orally injecting, surgical insertion via a vein or artery, an endoscopic procedure, or a lap aroscopic procedure. According to an embodiment, while a single apparatus 204 is shown in FIG. 2, example systems may include a plurality of apparatuses.

Accordingly, the apparatus 204, the local computing device 206, and/or the remote computing system 208 can be programed to execute computer instructions with respect the device orientation engine 101. As an example, the memory 224 stores these instructions for execution by the processor 222 so that the apparatus 204 can receive and process the biometric data via the biometric sensor 201. In this way, the processor 222 and the memory 224 are representative of processors and memories of the local computing device 206 and/or the remote computing system 208.

The apparatus 204, local computing device 206, and/or the remote computing system 208 can be any combination of software and/or hardware that individually or collectively store, execute, and implement the device orientation engine 101 and functions thereof. Further, the apparatus 204, local computing device 206, and/or the remote computing system 208 can be an electronic, computer framework comprising and/or employing any number and combination of computing device and networks utilizing various communication technologies, as described herein. The apparatus 204, local computing device 206, and/or the remote computing system 208 can be easily scalable, extensible, and modular, with the ability to change to different services or reconfigure some features independently of others.

The networks 210 and 211 can be a wired network, a wireless network, or include one or more wired and wireless networks. According to an embodiment, the network 210 is an example of a short-range network (e.g., local area network (LAN), or personal area network (PAN)). Information can be sent, via the network 210, between the apparatus 204 and the local computing device 206 using any one of various short-range wireless communication protocols, such as Bluetooth, Wi-Fi, Zigbee, Z-Wave, near field communications (NFC), ultra-band, Zigbee, or infrared (IR). Further, the network 211 is an example of one or more of an Intranet, a local area network (LAN), a wide area network (WAN), a metropolitan area network (MAN), a direct connection or series of connections, a cellular telephone network, or any other network or medium capable of facilitating communication between the local computing device 206 and the remote computing system 208. Information can be sent, via the network 211, using any one of various long-range wireless communication protocols (e.g., TCP/IP, HTTP, 3G, 4G/LTE, or 5G/New Radio). Note that for either network 210 and 211 wired connections can be implemented using Ethernet, Universal Serial Bus (USB), RJ-11 or any other wired connection and wireless connections can be implemented using Wi-Fi, WiMAX, and Bluetooth, infrared, cellular networks, satellite or any other wireless connection methodology.

In operation, the apparatus 204 can continually or periodically obtain, monitor, store, process, and communicate via network 210 the biometric data associated with the patient 202. Further, the apparatus 204, local computing device 206, and/the remote computing system 208 are in communication through the networks 210 and 211 (e.g., the local computing device 206 can be configured as a gateway between the apparatus 204 and the remote computing system 208). For instance, the apparatus 204 can be an example of the system 100 of FIG. 1 configured to communicate with the local computing device 206 via the network 210. The local computing device 206 can be, for example, a stationary/standalone device, a base station, a desktop/laptop computer, a smart phone, a smartwatch, a tablet, or other device configured to communicate with other devices via networks 211 and 210. The remote computing system 208, implemented as a physical server on or connected to the network 211 or as a virtual server in a public cloud computing provider (e.g., Amazon Web Services (AWS)®) of the network 211, can be configured to communicate with the local computing device 206 via the network 211. Thus, the biometric data associated with the patient 202 can be communicated throughout the system 200.

Elements of the apparatus 224 are now described. The biometric sensor 221 may include, for example, one or more transducers configured to convert one or more environmental conditions into an electrical signal, such that different types of biometric data are observed/obtained/acquired. For example, the biometric sensor 221 can include one or more of an electrode (e.g., the electrode 111 of FIG. 1), a temperature sensor (e.g., thermocouple), a blood pressure sensor, a blood glucose sensor, a blood oxygen sensor, a pH sensor, an accelerometer, and a microphone.

The processor 222, in executing the device orientation engine 101, can be configured to receive, process, and manage the biometric data acquired by the biometric sensor 221, and communicate the biometric data to the memory 224 for storage and/or across the network 210 via the transceiver 225. Biometric data from one or more other apparatuses 204 can also be received by the processor 222 through the transceiver 225. Also, as described in more detail herein, the processor 222 may be configured to respond selectively to different tapping patterns (e.g., a single tap or a double tap) received from the UI sensor 223, such that different tasks of a patch (e.g., acquisition, storing, or transmission of data) can be activated based on the detected pattern. In some embodiments, the processor 222 can generate audible feedback with respect to detecting a gesture.

The UI sensor 223 includes, for example, a piezoelectric sensor or a capacitive sensor configured to receive a user input, such as a tapping or touching. For example, the UI sensor 223 can be controlled to implement a capacitive coupling, in response to tapping or touching a surface of the apparatus 204 by the patient 202. Gesture recognition may be implemented via any one of various capacitive types, such as resistive capacitive, surface capacitive, projected capacitive, surface acoustic wave, piezoelectric and infrared touching. Capacitive sensors may be disposed at a small area or over a length of the surface, such that the tapping or touching of the surface activates the monitoring device.

The memory 224 is any non-transitory tangible media, such as magnetic, optical, or electronic memory (e.g., any suitable volatile and/or non-volatile memory, such as random-access memory or a hard disk drive). The memory 224 stores the computer instructions for execution by the processor 222.

The transceiver 225 may include a separate transmitter and a separate receiver. Alternatively, the transceiver 225 may include a transmitter and receiver integrated into a single device.

In operation, the apparatus 204, utilizing the device orientation engine 101, observes/obtains the biometric data of the patient 202 via the biometric sensor 221, stores the biometric data in the memory, and shares this biometric data across the system 200 via the transceiver 225. The device orientation engine 101 can then utilize models, neural networks, ML, and/or AI to provide cardiac physicians and medical personnel a visual representation of an original catheter position in relation to a displaced catheter position following inadvertent catheter movements.

Figure 3:
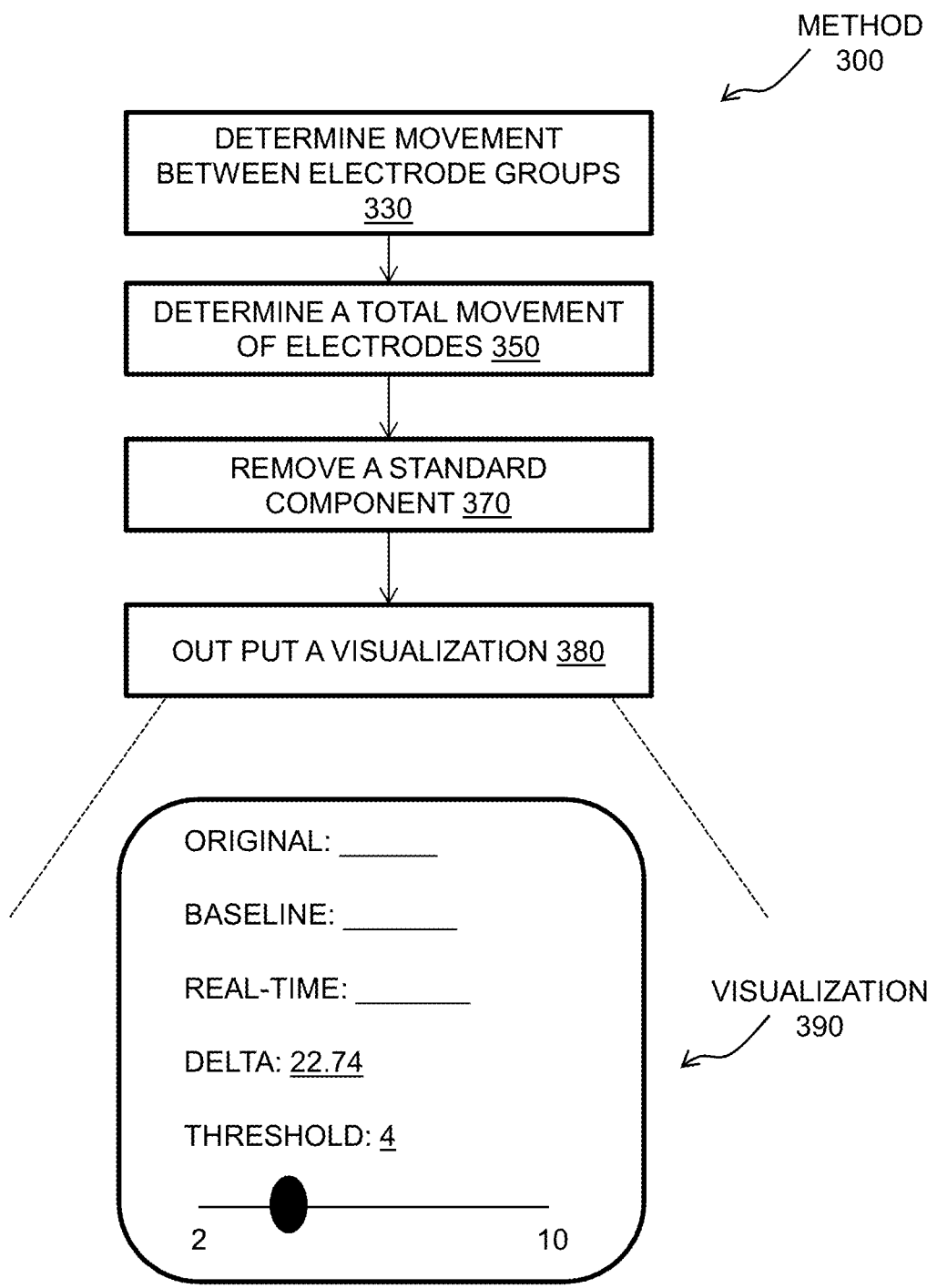
FIG. 3 illustrates an exemplary method according to one or more embodiments.

Turning now to FIG. 3, a method 300 (e.g., performed by the device orientation engine 101 of FIG. 1 and/or of FIG. 2) is illustrated according to one or more embodiments. The method 300 addresses a need for reliable measurements and mapping by providing a multi-step signal analysis of electrical signals, representing movements of a reference electrode of the catheter 110 in a CS vein, that enable an improved understanding an electrophysiology with more precision. In this example, the catheter 110 is a linear catheter with a plurality of electrodes 111. The plurality of electrodes 111 of the catheter 110 can be grouped (such as paired) and can provide position information over time.

The method begins at block 330, where the device orientation engine 101 determines a movement between each electrode group of the plurality of electrodes 111 of the catheter 110 to provide a plurality of movements. The electrode group can include two or more electrodes, such as pair, triplets, etc. The device orientation engine 101 utilizes the noted position information (e.g., positions per timestamp for electrodes 111 of each electrode group) and a reference position as inputs to determine the movement between each electrode group. According to an embodiment, the movement between each electrode group is determined based on at least a set of two vectors constructed for each electrode group and on a third vector between the set of two vectors for each electrode group.

At block 350, the device orientation engine 101 determines a total movement of the plurality of electrodes 111. The total movement can be based on an average movement of three median electrode pairs of the plurality of electrodes 111. For instance, the device orientation engine 101 determines a median value for each movement between each electrode pair, selects three movement measurements nearest to the median value to provide selected measurements, and determines an average value for the selected measurements to provide the average movement.

At block 370, the device orientation engine 101 removes a standard component from the plurality of movements and the total movement. The standard component comprises respiration movement and/or heartbeat movement (e.g., that can include gating, compensation, and/or the like).

At block 380, the device orientation engine 101 outputs a visualization 390 that includes movement indication for the catheter 110 based on the plurality of movements and the total movement with the standard component removed. The movement indication can be for every input position compared against a reference position and/or can be along an axial insertion axis of the catheter 110 into the CS.

The technical effects and benefits of the method 300 include enabling the cardiac physician to experience the visualization 390. The visualization 390 includes graphics enabling a correcting of axial movements along the CS, which affect the signals and timing of measurements (e.g., the plurality of movements and the total movement). More particularly, as shown in FIG. 3, the visualization 390 can indicate where the catheter 110 was originally (e.g., a baseline position), in relation to inadvertent catheter movements of the catheter 110, utilizing axial vector calculations to show a direction of the inadvertent catheter movements, relative to the baseline position. The measurements provided can be in any unit of length, such as millimeters.

That is, using the method 300, when the device orientation engine 101 detects catheter 110 movement along the CS, a dialogue box (e.g., the visualization 390) may provide an alert. The alert may indicate a threshold or delta threshold to show how far the catheter 110 moved (e.g., proximally or distally) from the baseline position. In this way, the dialogue box may show the baseline position versus the real-time position, particularly for the axial movement of the catheter 110 along the CS. With such alerts, the physician can decide whether to return the catheter 110 to the baseline position, using the delta value as a guide. Accordingly, the visualization 390 provides enhanced capability for tracking a position of the catheter 110, distinguishing between lateral and axial movements, and correcting inadvertent catheter movement along the CS.

Figure 4:
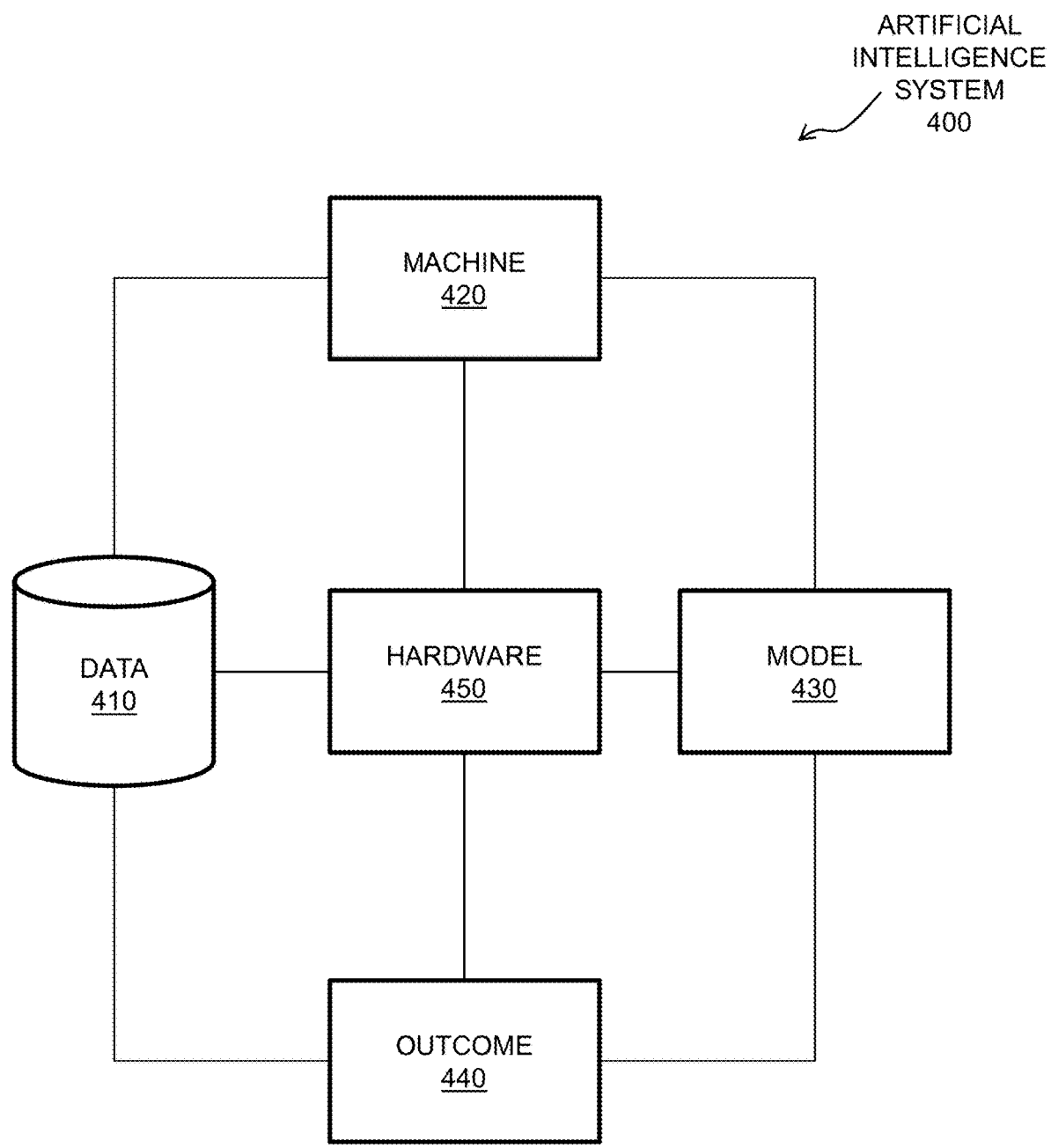
FIG. 4 illustrates a graphical depiction of an artificial intelligence system according to one or more embodiments.
Figure 5:
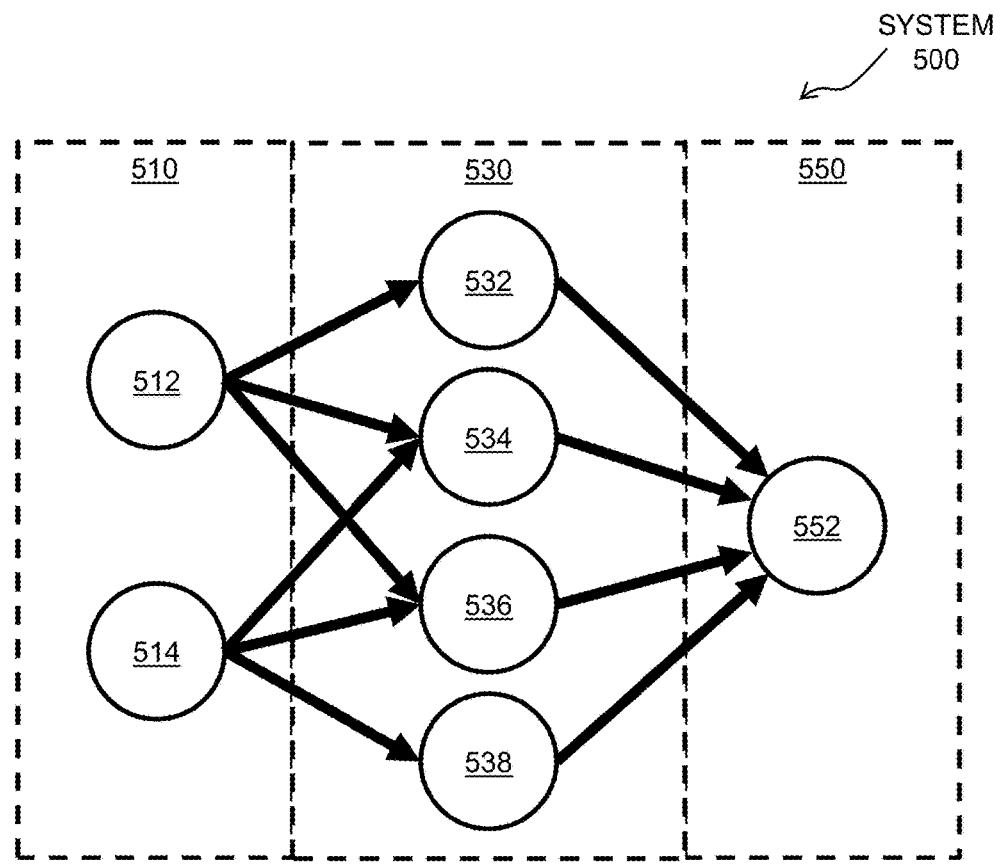
FIG. 5 illustrates an example of a neural network and a block diagram of a method performed in the neural network according to one or more embodiments.

FIG. 4 illustrates a graphical depiction of an AI system 400 according to one or more embodiments. The AI system 400 includes data 410 (e.g., biometric data), a machine 420, a model 430, an outcome 440, and (underlying) hardware 450. The description of FIGS. 4-5 is made with reference to FIGS. 1-3 for ease of understanding where appropriate. For example, the machine 420, the model 430, and the hardware 450 can represent aspects of the device orientation engine 101 of FIGS. 1-2 (e.g., the ML/AI algorithms therein), while the hardware 450 can also represent the catheter 110 of FIG. 1, the console 160 of FIG. 1, and/or the apparatus 204 of FIG. 2. In general, the ML/AI algorithms of the AI system 400 (e.g., as implemented by the device orientation engine 101 of FIGS. 1-2) operate with respect to the hardware 450, using the data 410, to train the machine 420, build the model 430, and predict the outcomes 440.

For instance, the machine 420 operates as the controller or data collection associated with the hardware 450 and/or is associated therewith. The data 410 (e.g., the biometric data as described herein) can be on-going data or output data associated with the hardware 450. The data 410 can also include currently collected data, historical data, or other data from the hardware 450; can include measurements during a surgical procedure and may be associated with an outcome of the surgical procedure; can include a temperature of the heart 120 of FIG. 1 collected and correlated with an outcome of a heart procedure; and can be related to the hardware 450. The data 410 can be divided by the machine 420 into one or more subsets.

Further, the machine 420 trains, such as with respect to the hardware 450. This training can also include an analysis and correlation of the data 410 collected. For example, in the case of the heart, the data 410 of temperature and outcome may be trained to determine if a correlation or link exists between the temperature of the heart 120 of FIG. 1 during the heart procedure and the outcome. In accordance with another embodiment, training the machine 420 can include self-training by the device orientation engine 101 of FIG. 1 utilizing the one or more subsets. In this regard, the device orientation engine 101 of FIG. 1 learns to detect case classifications on a point by point basis.

Moreover, the model 430 is built on the data 410 associated with the hardware 450. Building the model 430 can include physical hardware or software modeling, algorithmic modeling, and/or the like that seeks to represent the data 410 (or subsets thereof) that has been collected and trained. In some aspects, building of the model 430 is part of self-training operations by the machine 420. The model 430 can be configured to model the operation of hardware 450 and model the data 410 collected from the hardware 450 to predict the outcome 440 achieved by the hardware 450. Predicting the outcomes 440 (of the model 430 associated with the hardware 450) can utilize a trained model 430. For example and to increase understanding of the disclosure, in the case of the heart, if the temperature during the procedure that is between 36.5 degrees Celsius and 37.89 degrees Celsius (i.e., 97.7 degrees Fahrenheit and 100.2 degrees Fahrenheit) produces a positive result from the heart procedure, the outcome 440 can be predicted in a given procedure using these temperatures. Thus, using the outcome 440 that is predicted, the machine 420, the model 430, and the hardware 450 can be configured accordingly.

Thus, for the AI system 400 to operate with respect to the hardware 450, using the data 410, to train the machine 420, build the model 430, and predict the outcomes 440, the ML/AI algorithms therein can include neural networks. In general, a neural network is a network or circuit of neurons, or in a modern sense, an artificial neural network (ANN), composed of artificial neurons or nodes or cells.

For example, an ANN involves a network of processing elements (artificial neurons) which can exhibit complex global behavior, determined by the connections between the processing elements and element parameters. These connections of the network or circuit of neurons are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1.

In most cases, the ANN is an adaptive system that changes its structure based on external or internal information that flows through the network.

In more practical terms, neural networks are non-linear statistical data modeling or decision-making tools that can be used to model complex relationships between inputs and outputs or to find patterns in data. Thus, ANNs may be used for predictive modeling and adaptive control applications, while being trained via a dataset. Note that self-learning resulting from experience can occur within ANNs, which can derive conclusions from a complex and seemingly unrelated set of information. The utility of artificial neural network models lies in the fact that they can be used to infer a function from observations and also to use it. Unsupervised neural networks can also be used to learn representations of the input that capture the salient characteristics of the input distribution, and more recently, deep learning algorithms, which can implicitly learn the distribution function of the observed data. Learning in neural networks is particularly useful in applications where the complexity of the data (e.g., the biometric data) or task (e.g., monitoring, diagnosing, and treating any number of various diseases) makes the design of such functions by hand impractical.

Neural networks can be used in different fields. Thus, for the AI system 400, the ML/AI algorithms therein can include neural networks that are divided generally according to tasks to which they are applied. These divisions tend to fall within the following categories: regression analysis (e.g., function approximation) including time series prediction and modeling; classification including pattern and sequence recognition; novelty detection and sequential decision making; data processing including filtering; clustering; blind signal separation, and compression. For example, Application areas of ANNs include nonlinear system identification and control (vehicle control, process control), game-playing and decision making (backgammon, chess, racing), pattern recognition (radar systems, face identification, object recognition), sequence recognition (gesture, speech, handwritten text recognition), medical diagnosis and treatment, financial applications, data mining (or knowledge discovery in databases, "KDD"), visualization and e-mail spam filtering. For example, it is possible to create a semantic profile of patient biometric data emerging from medical procedures.

According to one or more embodiments, the neural network can implement a long short-term memory neural network architecture, a convolutional neural network (CNN) architecture, or other the like. The neural network can be configurable with respect to a number of layers, a number of connections (e.g., encoder/decoder connections), a regularization technique (e.g., dropout); and an optimization feature.

The long short-term memory neural network architecture includes feedback connections and can process single data points (e.g., such as images), along with entire sequences of data (e.g., such as speech or video). A unit of the long short-term memory neural network architecture can be composed of a cell, an input gate, an output gate, and a forget gate, where the cell remembers values over arbitrary time intervals and the gates regulate a flow of information into and out of the cell.

The CNN architecture is a shared-weight architecture with translation invariance characteristics where each neuron in one layer is connected to all neurons in the next layer. The regularization technique of the CNN architecture can take advantage of the hierarchical pattern in data and assemble more complex patterns using smaller and simpler patterns. If the neural network implements the CNN architecture, other configurable aspects of the architecture can include a number of filters at each stage, kernel size, a number of kernels per layer.

Turning now to FIG. 5, an example of a neural network 500 and a block diagram of a method 501 performed in the neural network 500 are shown according to one or more embodiments. The neural network 500 operates to support implementation of the ML/AI algorithms (e.g., as implemented by the device orientation engine 101 of FIGS. 1-2) described herein. The neural network 500 can be implemented in hardware, such as the machine 420 and/or the hardware 450 of FIG. 4. As indicated herein, the description of FIGS. 4-5 is made with reference to FIGS. 1-3 for ease of understanding where appropriate.

In an example operation, the device orientation engine 101 of FIG. 1 includes collecting the data 410 from the hardware 450. In the neural network 500, an input layer 510 is represented by a plurality of inputs (e.g., inputs 512 and 514 of FIG. 5). With respect to block 520 of the method 501, the input layer 510 receives the inputs 512 and 514. The inputs 512 and 514 can include biometric data. For example, the collecting of the data 410 can be an aggregation of biometric data (e.g., BS ECG data, IC ECG data, and ablation data, along with catheter electrode position data), from one or more procedure recordings of the hardware 450 into a dataset (as represented by the data 410).

At block 525 of the method 501, the neural network 500 encodes the inputs 512 and 514 utilizing any portion of the data 410 (e.g., the dataset and predictions produced by the AI system 400) to produce a latent representation or data coding. The latent representation includes one or more intermediary data representations derived from the plurality of inputs. According to one or more embodiments, the latent representation is generated by an element-wise activation function (e.g., a sigmoid function or a rectified linear unit) of the device orientation engine 101 of FIG. 1. As shown in FIG. 5, the inputs 512 and 514 are provided to a hidden layer 530 depicted as including nodes 532, 534, 536, and 538. The neural network 500 performs the processing via the hidden layer 530 of the nodes 532, 534, 536, and 538 to exhibit complex global behavior, determined by the connections between the processing elements and element parameters. Thus, the transition between layers 510 and 530 can be considered an encoder stage that takes the inputs 512 and 514 and transfers it to a deep neural network (within the hidden layer 530) to learn some smaller representation of the input (e.g., a resulting the latent representation).

The deep neural network can be a CNN, a long short-term memory neural network, a fully connected neural network, or combination thereof. The inputs 512 and 514 can be intracardiac ECG, body surface ECG, or intracardiac ECG and body surface ECG. This encoding provides a dimensionality reduction of the inputs 512 and 514. Dimensionality reduction is a process of reducing the number of random variables (of the inputs 512 and 514) under consideration by obtaining a set of principal variables. For instance, dimensionality reduction can be a feature extraction that transforms data (e.g., the inputs 512 and 514) from a high-dimensional space (e.g., more than 10 dimensions) to a lower-dimensional space (e.g., 2-3 dimensions). The technical effects and benefits of dimensionality reduction include reducing time and storage space requirements for the data 410, improving visualization of the data 410, and improving parameter interpretation for ML. This data transformation can be linear or nonlinear. The operations of receiving (block 520) and encoding (block 525) can be considered a data preparation portion of the multi-step data manipulation by the device orientation engine 101.

At block 545 of the method 501, the neural network 500 decodes the latent representation. The decoding stage takes the encoder output (e.g., the resulting the latent representation) and attempts to reconstruct some form of the inputs 512 and 514 using another deep neural network. In this regard, the nodes 532, 534, 536, and 538 are combined to produce in the output layer 550 an output 552, as shown in block 560 of the method 501. That is, the output layer 590 reconstructs the inputs 512 and 514 on a reduced dimension but without the signal interferences, signal artifacts, and signal noise. Examples of the output 552 include cleaned biometric data (e.g., clean/denoised version of IC ECG data or the like). The technical effects and benefits of the cleaned biometric data include enabling more accurate monitor, diagnosis, and treatment any number of various diseases.

Figure 6:
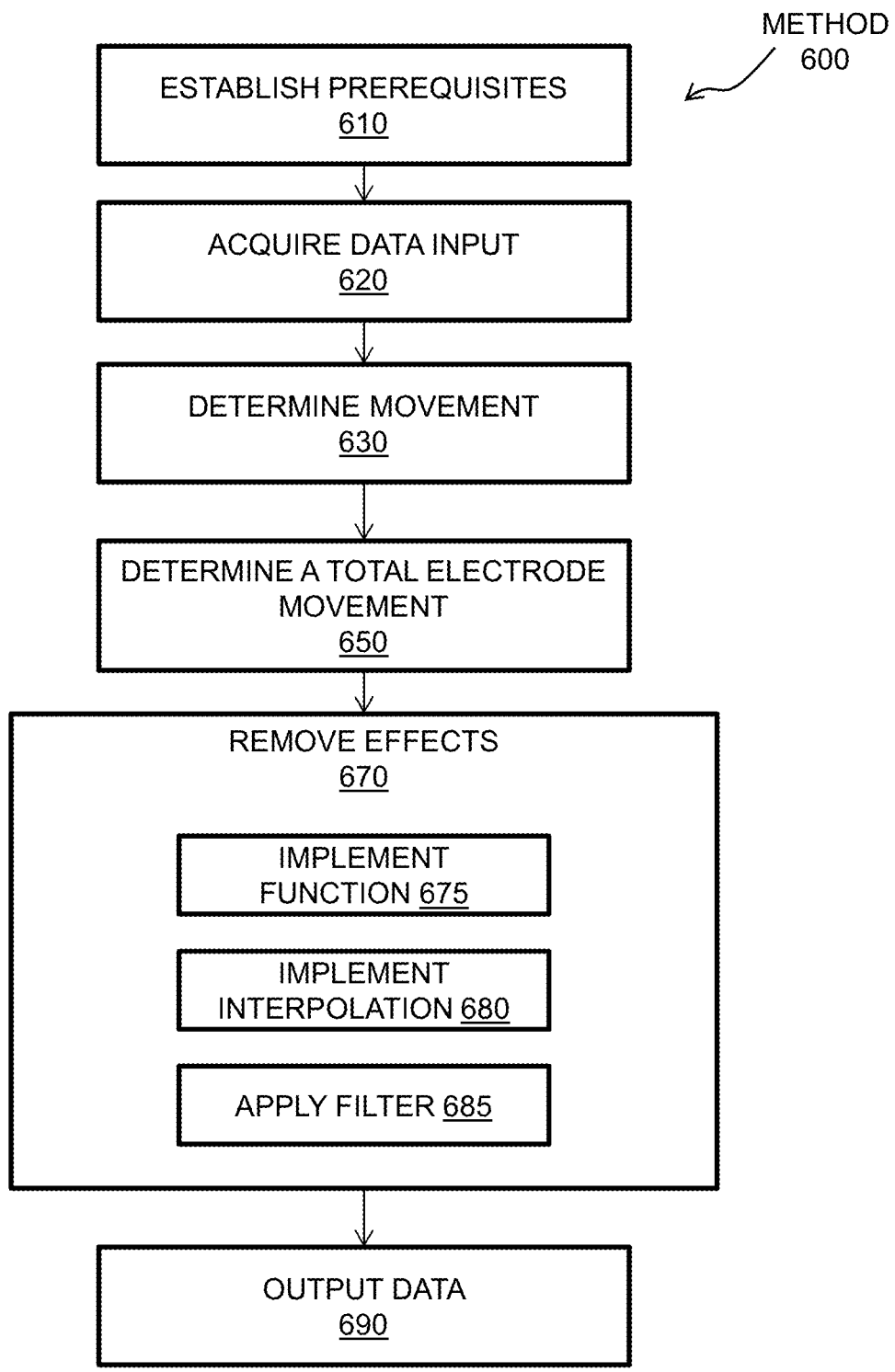
FIG. 6 illustrates an exemplary method according to one or more embodiments.

Turning now to FIG. 6, a method 600 (e.g., performed by the device orientation engine 101 of FIG. 1 and/or of FIG. 2) is illustrated according to one or more embodiments. FIG. 6 is described with reference to FIGS. 1 and 7-12 for ease or understanding and brevity.

The method 600 addresses a need for understanding and visualizing whether reference electrodes (e.g., of the plurality of electrodes 111 of the catheter 110) within the CS have moved due to a patient's respiration or heart beats. Further, when relying on the electrodes 111 as reference points within the CS, it is important that the electrodes do not move, otherwise the timing of the atrial tachycardia (AT) measurements are unreliable. Note that respiration and heart beats occur all through mapping and are not necessarily a sign of movement of the catheter 110. Moreover, in some cases, the device orientation engine 101 filters respiration and heart beats to obtain an indication of movements that are on the axial insertion axis of the catheter 110. In turn, the device orientation engine 101 allows relocation of the catheter 110 to a baseline position, which avoids re-mapping and prevents prolonging ay procedures.

The method 600 begins at block 610, where the device orientation engine 101 establishes prerequisites. Prerequisites can include one or more inputs and/or assumptions. For example, the device orientation engine 101 aims to detect movement of a linear catheter (e.g., the catheter 110), along an axial insertion axis of into the CS. An input includes positions of the electrodes 111. The device orientation engine 101 does not assume a use of a navigational diagnostic catheter and can be activated without a magnetic sensor input. An input also includes a reference position of the catheter 110 against which movements are measured. Next, the device orientation engine 101 proceeds with a movement calculation.

At block 620, the device orientation engine 101 acquires input data. Input data can include a position of an electrode per timestamp. Input data can also include (or in the alternative) a reference position for movement comparison.

At block 630, the device orientation engine 101 determines a movement of individual pairs of electrodes (e.g., to begin the determination of a movement of the catheter 110 along the axial axis is then calculated). According to an embodiment, the movement of each pair of electrodes is calculated between a reference position and a current position (e.g., a real-time position).

Figure 7:
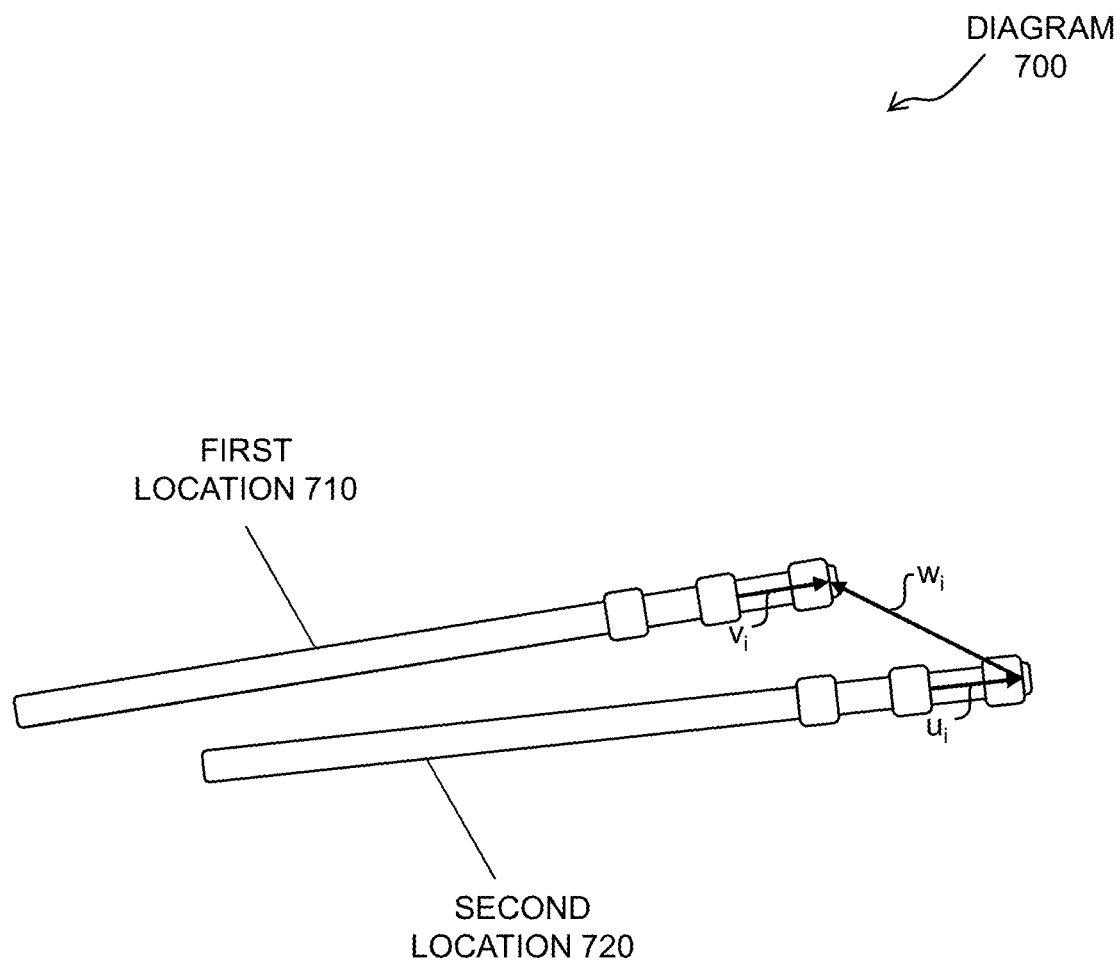
FIG. 7 illustrates a diagram a vector determination according to one or more embodiments.

Turning now to FIG. 7, a diagram 700 of a vector determination is illustrated according to one or more embodiments. Note that the device orientation engine 101, when making the vector determination, leverages of natural curvature of the CS. A set of two vectors are constructed for every adjacent pair of electrodes, based on the two locations (e.g., a first location 710 and a second location 720, as shown) of the catheter 110. The set of two vectors includes a first vector $\vec{u_1}$ for the reference position and a second vector $\vec{v_1}$ for the current position. An additional vector $\vec{w_1}$ is calculated between $\vec{u_1}$ and $\vec{v_1}$. The device orientation engine 101 determines a magnitude of vector $\vec{u_1}(\{x_1,y_1,z_1\}, \{x_2,y_2,z_2\})$ according to Equation 1 and determines an axial movement (measured in millimeters or mm) of each pair of electrodes using a dot product according to Equation 2.

$$\|u_i\| = \sqrt{(x_2 - x_1)^2 + (y_2 - y_1)^2 + (z_2 - z_1)^2} \quad \text{Equation 1}$$

$$\Delta_i = \frac{\vec{u_i} \cdot \vec{w_i}}{\|u_i\|} \quad \text{Equation 2}$$

At block 650, the device orientation engine 101 determines a total electrode movement. For example, once the movements have been calculated for each pair of adjacent electrodes, the movement of all electrodes can be calculated based on the average movement of the three median pairs, to remove effects of noise. According to an embodiment, a median value is determined by the device orientation engine 101 for all calculated movements of the paired electrodes. Then, the three nearest movement measurements $\Delta_i$ near the median value are selected by the device orientation engine 101. The device orientation engine 101, next, calculates an average value for the selected measurements according to Equation 3.

$$\Delta_{total} = \sum\nolimits_{(3\Delta_i \text{nearest to median})} \Delta_i / 3 \quad \text{Equation 5}$$

Figure 8:
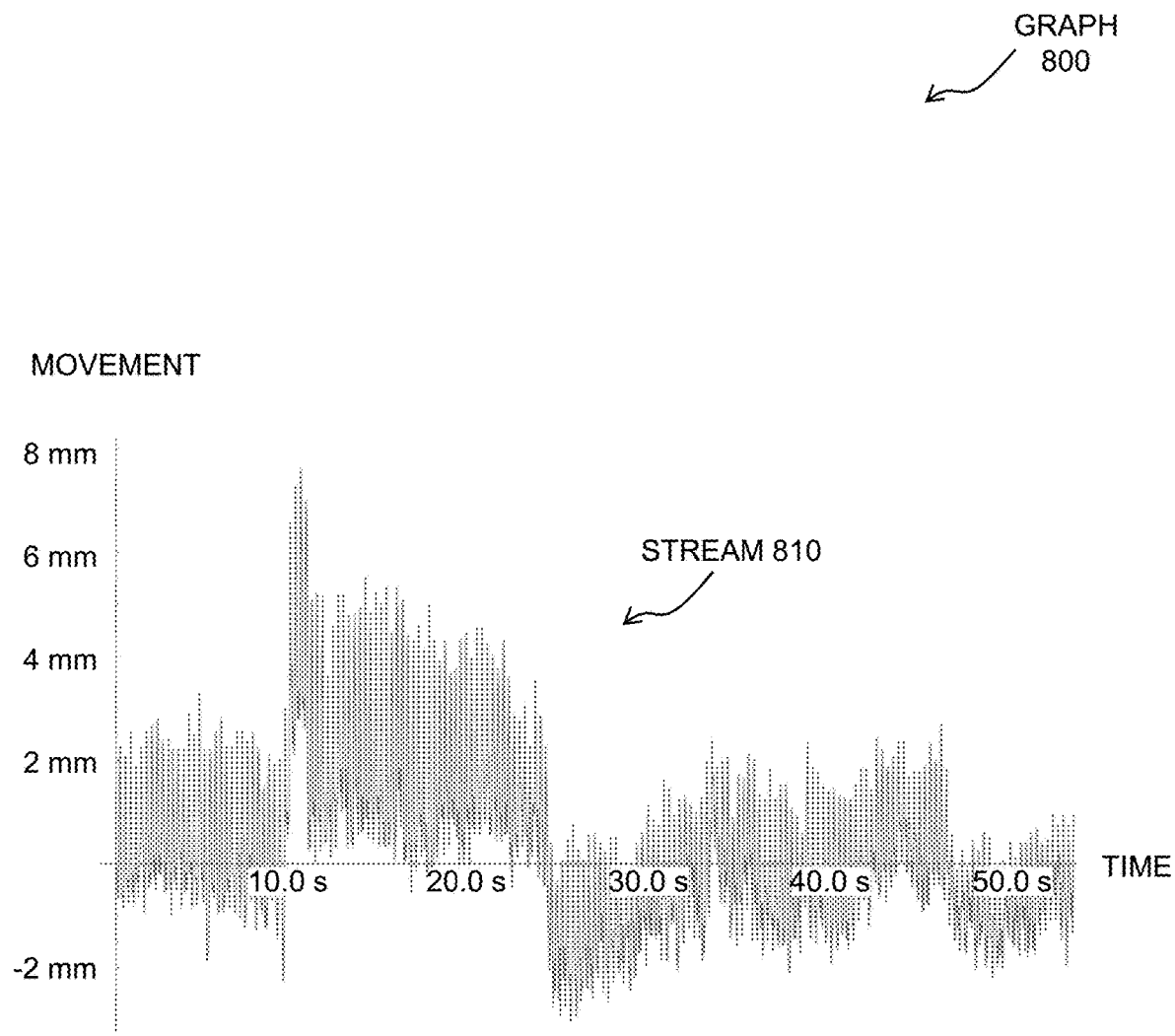
FIG. 8 illustrates a graph of movement overtime according to one or more embodiments.

At block 670, the device orientation engine 101 removes total respiration and heart beat effects. That is, because any calculated movements of the electrodes 111 can be affected by respiration and heartbeat movements (e.g., which are irrelevant to reference stability), the device orientation engine 101 implements an additional layer of processing remove these effects from any movement indications. The device orientation engine 101 relies on an output of an electrodes movement to include a low frequency and a high frequency due to respiration and heartbeat, respectively. FIG. 8 illustrates a graph 800 of movement over time according to one or more embodiments. Movement over time can be measured in millimeters or mm and can be considered a movement distances stream 810.

Figure 9:
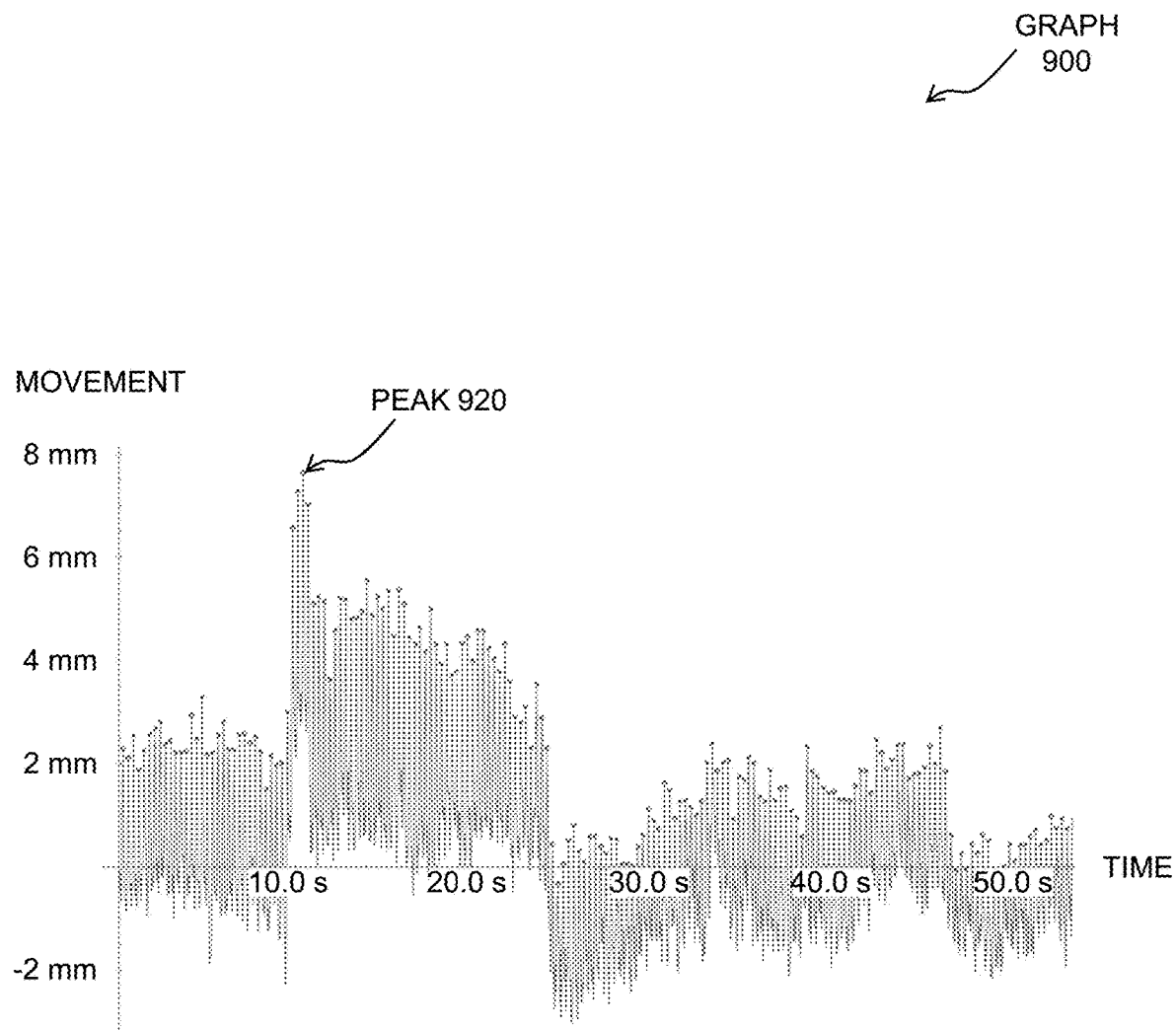
FIG. 9 illustrates a graph of peaks detection according to one or more embodiments.

At sub-block 675, the device orientation engine 101 implements a find peaks function on the movement distances stream 810 to allocate the peaks of the low frequency, representing of respiration. According to an embodiment, the find peaks function includes defining a moving window (e.g., a size of 361 samples) and calculating a maximum value for each step in a current window. FIG. 9 illustrates a graph 900 of peaks detection according to one or more embodiments. For instance, wherever the maximum value is located within the current window, that index is then indicated as a peak 920 (e.g., can be said to be at position 78) or peak index.

Figure 10:
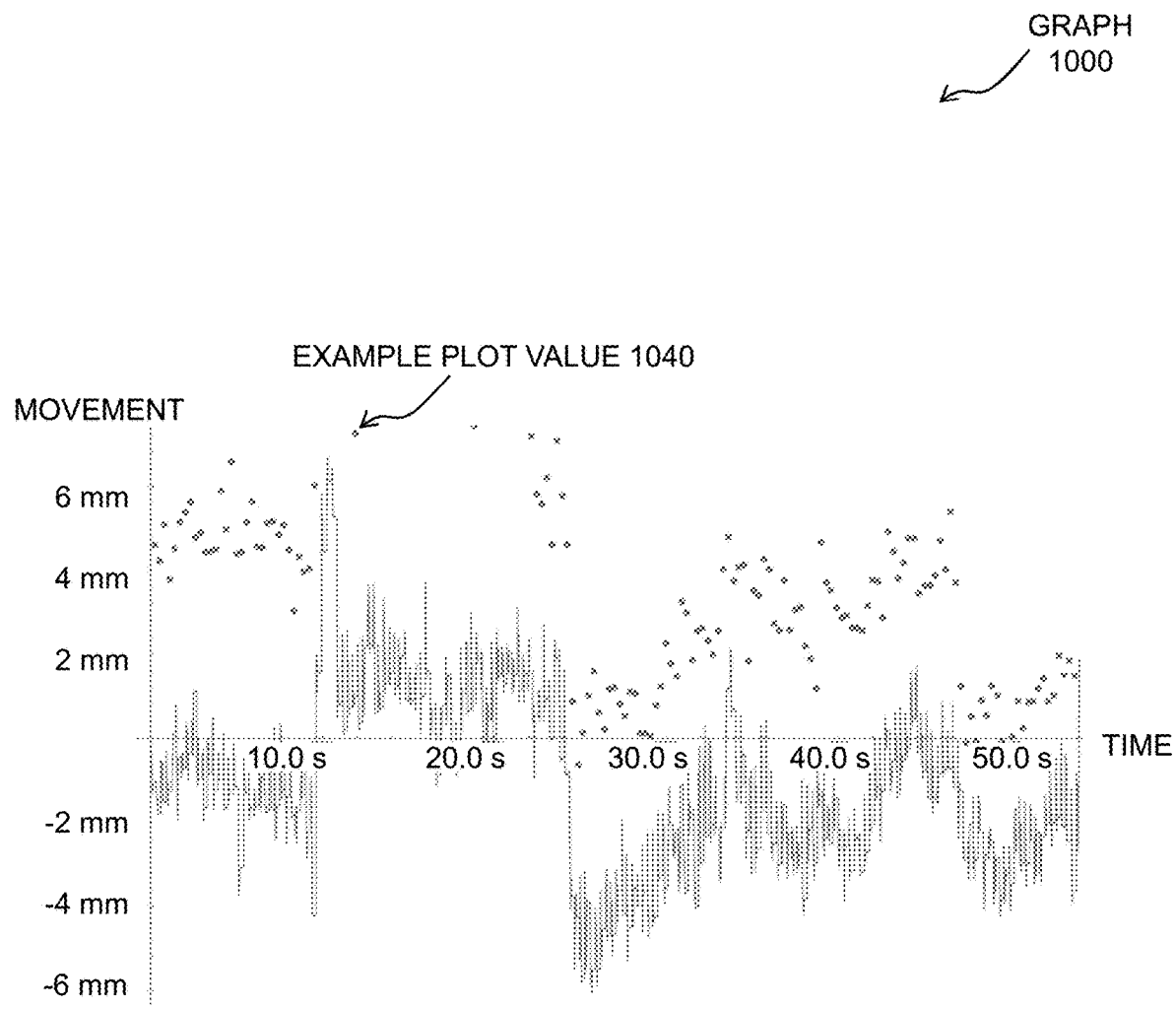
FIG. 10 illustrates a graph of a plot after interpolation according to one or more embodiments.

At sub-block 680, the device orientation engine 101 implements an interpolation around each identified peak. FIG. 10 illustrates a graph 1000 of a plot after interpolation according to one or more embodiments. That is, per each peak, an interpolation value is determined using a plot value (e.g., example plot value 1040) at a number of samples (e.g., 100 samples) before the peak index. For example, the interpolation value is then set for 100 samples before and 100 samples after the peak index. The interpolation results in a filtering of the low frequency.

Figure 11:
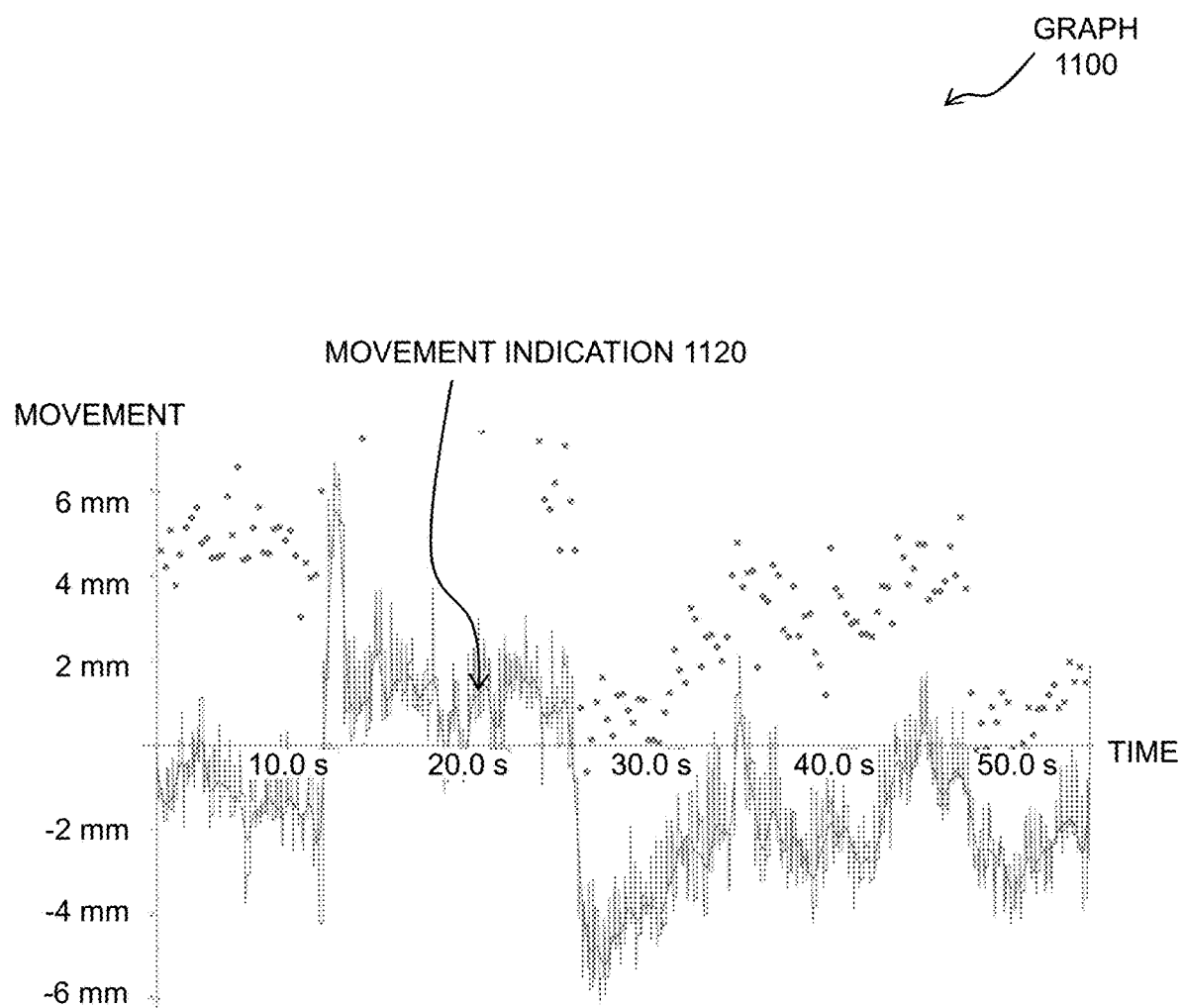
FIG. 11 illustrates a graph of a movement indication after utilizing a low pass filter according to one or more embodiments.

At sub-block 685, the device orientation engine 101 applies a low pass filter to smooth the high frequency and remove the heartbeat effect, using a cutoff frequency of 0.005. FIG. 11 illustrates a graph 1100 of a movement indication 1120 after utilizing a low pass filter according to one or more embodiments.

At block 690, the device orientation engine 101 provides output data. The output data includes a movement indication (mm) for every input position, compared against the reference position. The output data can identify movements, alert cardiac physicians and medical personnel, provide one or more actions including regain position, and provide information to reposition. Note that cardiac physicians and medical personnel can then manual reposition the catheter 110.

Figure 12:
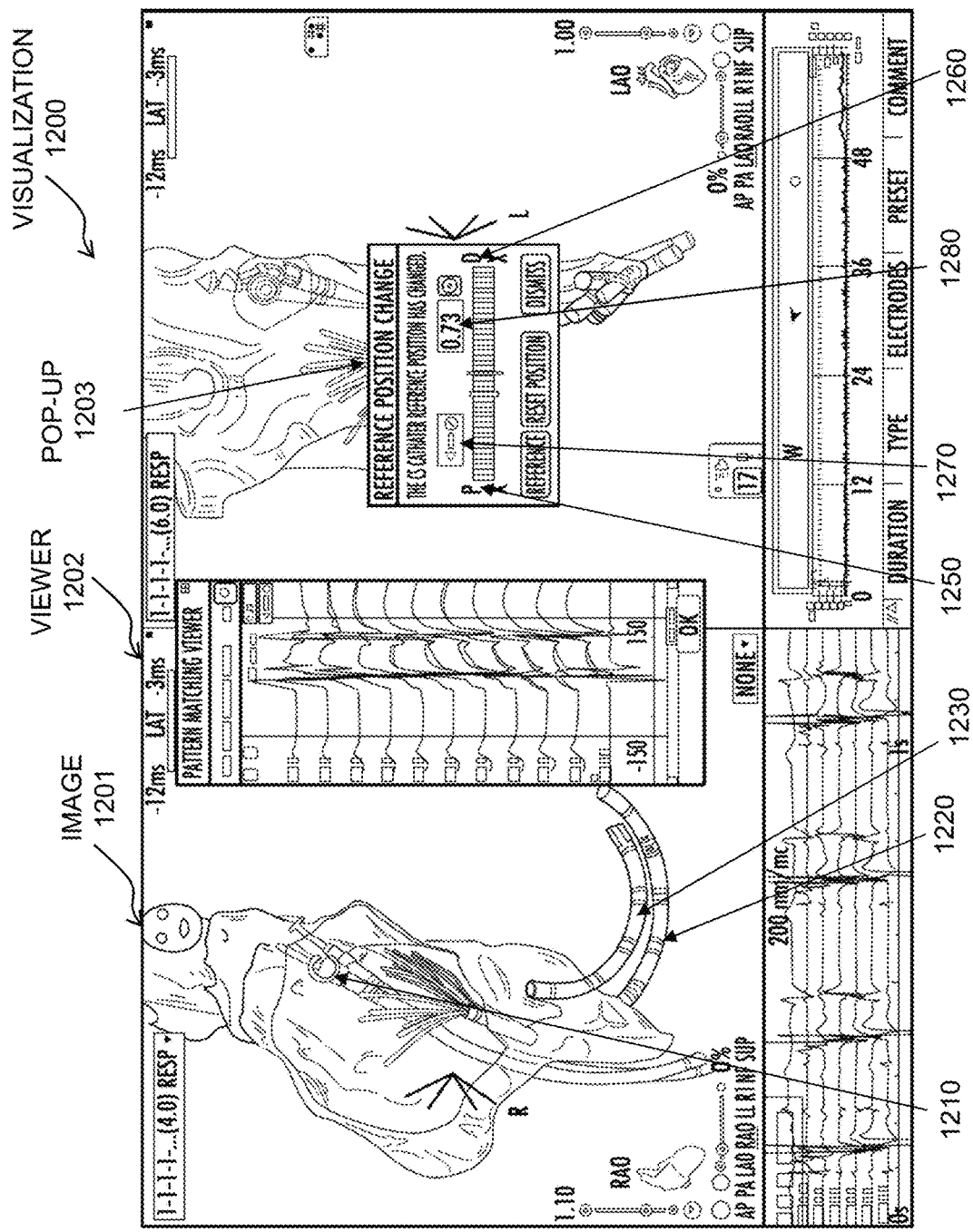
FIG. 12 illustrates a visualization according to one or more embodiments.

FIG. 12 illustrates a visualization 1200 according to one or more embodiments. According to an embodiment, the orientation engine 101 can implement pattern matching, accommodating any significance of movement on a morphology of the electrical signals, which is used to calculate the reference positions. That is, once the catheter 110 has been repositioned to an initial position, the orientation engine 101 ensures that the catheter 110 regains a same pattern of electrical signals (e.g., which could be different due to a tissue touched). For that reason, the orientation engine 101 can provide correlation with an original signal pattern, as seen in the visualization 1200.

More particularly, the visualization 1200 shows an image 1201, a viewer 1202, and a pop-up 1203. The image 1201 can be a three dimensional image mapping of a CS vein, where movements of the catheter 110 are shown with respect to a reference point 1210 as the catheter 110 moves between positions 1220 and 1230. That is, when repositioning the catheter 110 using a distance indication and a signals correlation value, a mapping (e.g., the image 1201) can be continued with high confidence of a stable reference. Further, IC pattern matching can be integrated or supplemented to the image 1201. In this way, the viewer 1202 can be provided as a pattern matching viewer. The IC pattern matching can be part of a calculation of movement, part of a correlation, supplementary to a whole process (e.g., when you have a movement of the catheter), and/or combination thereof. The pop-up 1203 provides a scale indicating a −/+ in the position change (mm) with respect to proximal 1250 and distal 1260 movements. Further, an amount of movement 1270 is shown, as well as a confidence 1280.

According to one or more embodiments, the device orientation engine 101 provides leverages the CS as an optimal reference point because temporal patterns of CS activations can be helpful in mapping. The analysis by the device orientation engine 101 of the temporal patterns of the CS activations provides a rapid stratification, or ordering, of most likely macro-reentrant ATs, and the analysis also points toward the likely origin of focal ATs. Therefore, the device orientation engine 101 provides the technical effect and benefits of detecting CS catheter movement and analyzing such movement with a visual or graphical representation, to assist the cardiac physicians and medical personnel in repositioning the catheter 110 along the CS. Thus, the cardiac physicians and medical personnel could either reposition the catheter 110 to the original position or otherwise to a new baseline position, to start a new mapping.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   determining, by a device orientation engine executed by one or more processors, a movement between each electrode group of a plurality of electrodes of a catheter to provide a plurality of movements, each electrode group comprising at least two adjacent electrodes;
   determining, by the device orientation engine, a total movement of the plurality of electrodes;
   removing, by the device orientation engine, a standard component from the plurality of movements and the total movement after the plurality of movements are determined, the standard component comprising respiration movement and heartbeat movement; and
   outputting, by the device orientation engine, a movement indication for the catheter based on the plurality of movements and the total movement with the standard component removed.

2. The method of claim 1, the device orientation engine utilizing positions per timestamp for electrodes of each electrode group and a reference position as inputs for determining the movement between each electrode group.

3. The method of claim 1, the movement between each electrode group being determined based on at least a set of two vectors constructed for each electrode group.

4. The method of claim 3, the movement between each electrode group being determined based on a third vector between the set of two vectors for each electrode group.

5. The method of claim 1, the total movement being based on an average movement of three median electrode pairs of the plurality of electrodes.

6. The method of claim 5, the device orientation engine:
   determining a median value for each movement between each electrode pair;
   selecting three movement measurements nearest to the median value to provide selected measurements; and
   determining an average value for the selected measurements to provide the average movement.

7. The method of claim 1, the movement indication being for every input position compared against a reference position.

8. The method of claim 1, the movement indication being along an axial insertion axis of the catheter into a coronary sinus.

9. The method of claim 1, the catheter being a linear catheter.

10. A system comprising:
    a memory storing processor executable code for a device orientation engine; and
    one or more processors executing the processor executable code to cause the system to:
       determine, by the device orientation engine, a movement between each electrode group of a plurality of electrodes of a catheter to provide a plurality of movements, each electrode group comprising at least two adjacent electrodes,
       determine, by the device orientation engine, a total movement of the plurality of electrodes,
       remove, by the device orientation engine, a standard component from the plurality of movements and the total movement after the plurality of movements are determined, the standard component comprising any of respiration movement and heartbeat movement, and
       output, by the device orientation engine, a movement indication for the catheter based on the plurality of movements and the total movement with the standard component removed.

11. The system of claim 10, the device orientation engine utilizing positions per timestamp for electrodes of each electrode group and a reference position as inputs for determining the movement between each electrode group.

12. The system of claim 10, the movement between each electrode group being determined based on at least a set of two vectors constructed for each electrode group.

13. The system of claim 12, the movement between each electrode group being determined based on a third vector between the set of two vectors for each electrode group.

14. The system of claim 10, the total movement being based on an average movement of three median electrode pairs of the plurality of electrodes.

15. The system of claim 14, the processor executable code being further executed to cause the system to:
    determine a median value for each movement between each electrode pair;
    select three movement measurements nearest to the median value to provide selected measurements; and
    determine an average value for the selected measurements to provide the average movement.

16. The system of claim 10, the standard component comprising respiration movement and heartbeat movement.

17. The system of claim 10, the movement indication being for every input position compared against a reference position.

18. The system of claim 10, the movement indication being along an axial insertion axis of the catheter into a coronary sinus.

19. The system of claim 10, the catheter being a linear catheter.

* * * * *